(12) United States Patent
Hildebrand et al.

(10) Patent No.: US 8,668,734 B2
(45) Date of Patent: Mar. 11, 2014

(54) INTRAOCULAR LENS DELIVERY DEVICES AND METHODS OF USE

(75) Inventors: Daniel Hildebrand, San Francisco, CA (US); Claudio Argento, Los Gatos, CA (US); Gregory V. Matthews, San Francisco, CA (US)

(73) Assignee: PowerVision, Inc., Belmont, CA (US)

( * ) Notice: Subject to any disclaimer, the term of this patent is extended or adjusted under 35 U.S.C. 154(b) by 0 days.

(21) Appl. No.: 13/180,427

(22) Filed: Jul. 11, 2011

(65) Prior Publication Data

US 2012/0022547 A1 Jan. 26, 2012

Related U.S. Application Data

(60) Provisional application No. 61/363,155, filed on Jul. 9, 2010.

(51) Int. Cl.
*A61F 2/16* (2006.01)

(52) U.S. Cl.
USPC .......................................................... 623/6.12

(58) Field of Classification Search
USPC ................................. 606/107; 623/6.11, 6.12
See application file for complete search history.

(56) References Cited

U.S. PATENT DOCUMENTS

| | | |
|---|---|---|
| 4,111,995 A | 9/1978 | Nelson |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,600,004 A | 7/1986 | Lopez et al. |
| 4,604,295 A | 8/1986 | Humphreys |
| 4,615,701 A | 10/1986 | Woods |
| 4,620,954 A | 11/1986 | Singer et al. |
| 4,681,102 A | 7/1987 | Bartell |
| 4,685,921 A | 8/1987 | Peyman |
| 4,685,922 A | 8/1987 | Peyman |
| 4,693,717 A | 9/1987 | Michelson |

(Continued)

FOREIGN PATENT DOCUMENTS

| | | |
|---|---|---|
| EP | 0898972 A2 | 3/1999 |
| EP | 1356791 B1 | 4/2006 |

(Continued)

OTHER PUBLICATIONS

Matthews, Gregory V.; U.S. Appl. No. 13/427,617 entitled "Intraocular Lens Loading Systems and Methods of Use," filed Mar. 22, 2012.

(Continued)

*Primary Examiner* — Ryan Severson
*Assistant Examiner* — Jonathan W Miles
(74) *Attorney, Agent, or Firm* — Shay Glenn LLP

(57) ABSTRACT

Intraocular lens delivery devices and methods of use.

6 Claims, 11 Drawing Sheets

(56) References Cited

U.S. PATENT DOCUMENTS

| | | |
|---|---|---|
| 4,702,244 A | 10/1987 | Mazzocco |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,747,404 A | 5/1988 | Jampel et al. |
| 4,763,650 A | 8/1988 | Hauser |
| 4,764,423 A | 8/1988 | Yamaguchi et al. |
| 4,765,329 A | 8/1988 | Cumming et al. |
| 4,781,719 A | 11/1988 | Kelman |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,819,631 A | 4/1989 | Poley |
| 4,834,094 A | 5/1989 | Patton et al. |
| 4,836,201 A | 6/1989 | Patton et al. |
| 4,842,601 A | 6/1989 | Smith |
| 4,848,343 A | 7/1989 | Wallsten et al. |
| 4,862,885 A | 9/1989 | Cumming |
| 4,880,000 A | 11/1989 | Holmes et al. |
| 4,888,012 A | 12/1989 | Horn et al. |
| 4,892,543 A | 1/1990 | Turley |
| 4,902,293 A | 2/1990 | Feaster |
| 4,906,247 A | 3/1990 | Fritch |
| 4,911,158 A | 3/1990 | Weatherly |
| 4,911,714 A | 3/1990 | Poley |
| 4,917,680 A | 4/1990 | Poley |
| 4,919,130 A | 4/1990 | Stoy et al. |
| 4,919,151 A | 4/1990 | Grubbs et al. |
| 4,932,966 A | 6/1990 | Christie et al. |
| 4,934,363 A | 6/1990 | Smith et al. |
| 4,946,469 A | 8/1990 | Sarfarazi |
| 4,950,289 A | 8/1990 | Krasner |
| 4,955,889 A | 9/1990 | Van Gent |
| 4,963,148 A | 10/1990 | Sulc et al. |
| 4,988,352 A | 1/1991 | Poley |
| 4,994,082 A | 2/1991 | Richards et al. |
| 4,995,879 A | 2/1991 | Dougherty |
| 4,995,880 A | 2/1991 | Galib |
| 5,007,913 A | 4/1991 | Dulebohn et al. |
| 5,015,254 A | 5/1991 | Greite |
| 5,026,393 A | 6/1991 | Mackool |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,098,439 A | 3/1992 | Hill et al. |
| 5,100,410 A | 3/1992 | Dulebohn |
| 5,123,905 A | 6/1992 | Kelman |
| 5,145,884 A | 9/1992 | Yamamoto et al. |
| 5,145,935 A | 9/1992 | Hayashi |
| 5,152,789 A | 10/1992 | Willis |
| 5,171,241 A | 12/1992 | Buboltz et al. |
| 5,171,266 A | 12/1992 | Wiley et al. |
| 5,176,686 A | 1/1993 | Poley |
| 5,190,552 A | 3/1993 | Kelman |
| 5,200,430 A | 4/1993 | Federman |
| 5,201,763 A | 4/1993 | Brady et al. |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,304,182 A | 4/1994 | Rheinish et al. |
| 5,326,347 A | 7/1994 | Cumming |
| 5,354,333 A | 10/1994 | Kammann et al. |
| 5,391,590 A | 2/1995 | Gerace et al. |
| 5,405,386 A | 4/1995 | Rheinish et al. |
| 5,425,734 A | 6/1995 | Blake |
| 5,443,506 A | 8/1995 | Garabet |
| 5,444,106 A | 8/1995 | Zhou et al. |
| 5,444,135 A | 8/1995 | Cheradame et al. |
| 5,452,932 A | 9/1995 | Griffin |
| 5,468,246 A | 11/1995 | Blake |
| 5,474,562 A | 12/1995 | Orchowski et al. |
| 5,476,514 A | 12/1995 | Cumming |
| 5,489,302 A | 2/1996 | Skottun |
| 5,494,484 A | 2/1996 | Feingold |
| 5,496,328 A | 3/1996 | Nakajima et al. |
| 5,496,366 A | 3/1996 | Cumming |
| 5,499,987 A | 3/1996 | Feingold |
| 5,506,300 A | 4/1996 | Ward et al. |
| 5,512,609 A | 4/1996 | Yang |
| 5,549,614 A | 8/1996 | Tunis |
| 5,556,400 A | 9/1996 | Tunis |
| 5,562,676 A | 10/1996 | Brady et al. |
| 5,578,081 A | 11/1996 | McDonald |
| 5,582,613 A | 12/1996 | Brady et al. |
| 5,584,304 A | 12/1996 | Brady |
| 5,585,049 A | 12/1996 | Grisoni et al. |
| 5,593,436 A | 1/1997 | Langerman |
| 5,607,433 A | 3/1997 | Polla et al. |
| 5,607,472 A | 3/1997 | Thompson |
| 5,616,148 A | 4/1997 | Eagles et al. |
| 5,620,450 A | 4/1997 | Eagles et al. |
| 5,628,795 A | 5/1997 | Langerman |
| 5,633,504 A | 5/1997 | Collins et al. |
| 5,643,276 A | 7/1997 | Zaleski |
| 5,653,715 A | 8/1997 | Reich et al. |
| 5,665,822 A | 9/1997 | Bitler et al. |
| 5,674,282 A | 10/1997 | Cumming |
| 5,697,973 A | 12/1997 | Peyman et al. |
| 5,702,400 A | 12/1997 | Brown et al. |
| 5,702,402 A | 12/1997 | Brady |
| 5,702,441 A | 12/1997 | Zhou |
| 5,716,364 A | 2/1998 | Makker et al. |
| 5,735,858 A | 4/1998 | Makker et al. |
| 5,766,182 A | 6/1998 | McDonald |
| 5,772,666 A | 6/1998 | Feingold et al. |
| 5,774,273 A | 6/1998 | Bornhorst |
| 5,776,138 A | 7/1998 | Vidal et al. |
| 5,776,191 A | 7/1998 | Mazzocco |
| 5,776,192 A | 7/1998 | McDonald |
| 5,800,442 A | 9/1998 | Wolf et al. |
| 5,803,925 A | 9/1998 | Yang et al. |
| 5,810,834 A | 9/1998 | Heyman |
| 5,843,188 A | 12/1998 | McDonald |
| 5,860,984 A | 1/1999 | Chambers et al. |
| 5,868,751 A | 2/1999 | Feingold |
| 5,873,879 A | 2/1999 | Figueroa et al. |
| 5,876,440 A | 3/1999 | Feingold |
| 5,891,931 A | 4/1999 | Leboeuf et al. |
| 5,919,197 A | 7/1999 | McDonald |
| 5,921,989 A | 7/1999 | Deacon et al. |
| 5,928,282 A | 7/1999 | Nigam |
| 5,941,886 A | 8/1999 | Feingold |
| 5,944,725 A | 8/1999 | Cicenas et al. |
| 5,947,974 A | 9/1999 | Brady et al. |
| 5,947,975 A | 9/1999 | Kikuchi et al. |
| 5,947,976 A | 9/1999 | Van Noy et al. |
| 5,964,802 A | 10/1999 | Anello et al. |
| 5,976,150 A | 11/1999 | Copeland |
| 5,984,962 A | 11/1999 | Anello et al. |
| 6,001,107 A | 12/1999 | Feingold |
| 6,010,510 A | 1/2000 | Brown et al. |
| 6,013,101 A | 1/2000 | Israel |
| 6,015,842 A | 1/2000 | LeBoeuf et al. |
| 6,022,358 A | 2/2000 | Wolf et al. |
| 6,048,348 A | 4/2000 | Chambers et al. |
| 6,059,791 A | 5/2000 | Chambers |
| 6,074,397 A | 6/2000 | Chambers et al. |
| 6,102,539 A | 8/2000 | Tucker |
| 6,117,171 A | 9/2000 | Skottun |
| 6,124,980 A | 9/2000 | Cerbell |
| 6,129,733 A | 10/2000 | Brady et al. |
| 6,139,576 A | 10/2000 | Doyle et al. |
| 6,143,000 A | 11/2000 | Feingold |
| 6,143,001 A | 11/2000 | Brown et al. |

(56) References Cited

U.S. PATENT DOCUMENTS

| | | | |
|---|---|---|---|
| 6,160,084 | A | 12/2000 | Langer et al. |
| 6,176,878 | B1 | 1/2001 | Gwon et al. |
| 6,179,843 | B1 | 1/2001 | Weiler |
| 6,180,687 | B1 | 1/2001 | Hammer et al. |
| 6,188,526 | B1 | 2/2001 | Sasaya et al. |
| 6,190,410 | B1 | 2/2001 | Lamielle et al. |
| 6,195,807 | B1 | 3/2001 | Chou |
| 6,197,059 | B1 | 3/2001 | Cumming |
| 6,217,612 | B1 | 4/2001 | Woods |
| 6,225,367 | B1 | 5/2001 | Chaouk et al. |
| 6,229,641 | B1 | 5/2001 | Kosaka |
| 6,241,737 | B1 | 6/2001 | Feingold |
| 6,248,111 | B1 | 6/2001 | Glick et al. |
| 6,251,114 | B1 | 6/2001 | Farmer et al. |
| 6,280,449 | B1 | 8/2001 | Blake |
| 6,283,975 | B1 | 9/2001 | Glick et al. |
| 6,283,976 | B1 | 9/2001 | Portney |
| 6,299,641 | B1 | 10/2001 | Woods |
| 6,302,911 | B1 | 10/2001 | Hanna |
| 6,312,433 | B1 | 11/2001 | Butts et al. |
| 6,322,589 | B1 | 11/2001 | Cumming |
| 6,334,862 | B1 | 1/2002 | Vidal et al. |
| 6,336,932 | B1 | 1/2002 | Figueroa et al. |
| 6,342,073 | B1 | 1/2002 | Cumming et al. |
| 6,348,437 | B1 | 2/2002 | Avery et al. |
| 6,371,960 | B2 | 4/2002 | Heyman et al. |
| 6,387,101 | B1 | 5/2002 | Butts et al. |
| 6,387,126 | B1 | 5/2002 | Cumming |
| 6,388,043 | B1 | 5/2002 | Langer et al. |
| 6,398,789 | B1 | 6/2002 | Capetan |
| 6,406,481 | B2 | 6/2002 | Feingold et al. |
| 6,406,494 | B1 | 6/2002 | Laguette et al. |
| 6,413,262 | B2 | 7/2002 | Saishin et al. |
| 6,423,094 | B1 | 7/2002 | Sarfarazi |
| 6,436,092 | B1 | 8/2002 | Peyman |
| 6,443,985 | B1 | 9/2002 | Woods |
| 6,447,520 | B1 | 9/2002 | Ott et al. |
| 6,450,642 | B1 | 9/2002 | Jethmalani et al. |
| 6,464,725 | B2 | 10/2002 | Skotton |
| 6,468,282 | B2 | 10/2002 | Kikuchi et al. |
| 6,471,708 | B2 | 10/2002 | Green |
| 6,488,708 | B2 | 12/2002 | Sarfarazi |
| 6,491,697 | B1 | 12/2002 | Clark et al. |
| 6,493,151 | B2 | 12/2002 | Schachar |
| 6,497,708 | B1 | 12/2002 | Cumming |
| 6,503,275 | B1 | 1/2003 | Cumming |
| 6,503,276 | B2 | 1/2003 | Lang et al. |
| 6,506,195 | B2 | 1/2003 | Chambers et al. |
| 6,517,577 | B1 | 2/2003 | Callahan et al. |
| 6,537,283 | B2 | 3/2003 | Van Noy |
| 6,551,354 | B1 | 4/2003 | Ghazizadeh et al. |
| 6,552,860 | B1 | 4/2003 | Alden |
| 6,554,859 | B1 | 4/2003 | Lang et al. |
| 6,585,768 | B2 | 7/2003 | Hamano et al. |
| 6,589,550 | B1 | 7/2003 | Hodd et al. |
| 6,592,621 | B1 | 7/2003 | Domino |
| 6,599,317 | B1 | 7/2003 | Weinschenk, III et al. |
| 6,601,956 | B1 | 8/2003 | Jean et al. |
| 6,605,093 | B1 | 8/2003 | Blake |
| 6,610,350 | B2 | 8/2003 | Suzuki et al. |
| 6,616,691 | B1 | 9/2003 | Tran |
| 6,616,692 | B1 | 9/2003 | Glick et al. |
| 6,638,304 | B2 | 10/2003 | Azar |
| 6,638,305 | B2 | 10/2003 | Laguette |
| 6,638,306 | B2 | 10/2003 | Cumming |
| 6,645,245 | B1 | 11/2003 | Preussner |
| 6,645,246 | B1 | 11/2003 | Weinschenk, III et al. |
| 6,656,223 | B2 | 12/2003 | Brady |
| 6,660,035 | B1 | 12/2003 | Lang et al. |
| 6,692,525 | B2 | 2/2004 | Brady et al. |
| 6,695,881 | B2 | 2/2004 | Peng et al. |
| 6,709,108 | B2 | 3/2004 | Levine et al. |
| 6,712,848 | B1 | 3/2004 | Wolf et al. |
| 6,723,104 | B2 | 4/2004 | Ott |
| 6,730,123 | B1 | 5/2004 | Klopotek |
| 6,733,507 | B2 | 5/2004 | McNicholas et al. |
| 6,743,388 | B2 | 6/2004 | Sridharan et al. |
| 6,749,632 | B2 | 6/2004 | Sandstedt et al. |
| 6,749,634 | B2 | 6/2004 | Hanna |
| 6,786,934 | B2 | 9/2004 | Zadno-Azizi et al. |
| 6,818,158 | B2 | 11/2004 | Pham et al. |
| 6,827,738 | B2 | 12/2004 | Willis et al. |
| 6,836,374 | B2 | 12/2004 | Esch et al. |
| 6,860,601 | B2 | 3/2005 | Shadduck |
| 6,878,320 | B1 | 4/2005 | Alderson et al. |
| 6,884,261 | B2 | 4/2005 | Zadno-Azizi et al. |
| 6,899,732 | B2 | 5/2005 | Zadno-Azizi et al. |
| 6,899,850 | B2 | 5/2005 | Haywood et al. |
| 6,914,247 | B2 | 7/2005 | Duggan et al. |
| 6,921,405 | B2 | 7/2005 | Feingold et al. |
| 6,923,815 | B2 | 8/2005 | Brady et al. |
| 6,926,736 | B2 | 8/2005 | Peng et al. |
| 6,935,743 | B2 | 8/2005 | Shadduck |
| 6,949,093 | B1 | 9/2005 | Peyman |
| 6,966,649 | B2 | 11/2005 | Shadduck |
| 6,969,403 | B2 | 11/2005 | Peng et al. |
| 7,001,374 | B2 | 2/2006 | Peyman |
| 7,014,641 | B2 | 3/2006 | Kobayashi et al. |
| 7,060,094 | B2 | 6/2006 | Shahinpoor et al. |
| 7,068,439 | B2 | 6/2006 | Esch et al. |
| 7,070,276 | B2 | 7/2006 | Koretz |
| 7,074,227 | B2 | 7/2006 | Portney |
| 7,122,053 | B2 | 10/2006 | Esch |
| 7,144,423 | B2 | 12/2006 | McDonald |
| 7,156,854 | B2 | 1/2007 | Brown et al. |
| 7,217,288 | B2 | 5/2007 | Esch et al. |
| 7,241,312 | B2 | 7/2007 | Lai et al. |
| 7,247,168 | B2 | 7/2007 | Esch et al. |
| 7,247,689 | B2 | 7/2007 | Makker et al. |
| 7,261,737 | B2 | 8/2007 | Esch et al. |
| 7,264,351 | B2 | 9/2007 | Shadduck |
| 7,276,619 | B2 | 10/2007 | Kunzler et al. |
| 7,278,739 | B2 | 10/2007 | Shadduck |
| 7,311,194 | B2 | 12/2007 | Jin et al. |
| 7,335,209 | B2 | 2/2008 | Meyer |
| 7,416,300 | B2 | 8/2008 | Wei et al. |
| 7,438,723 | B2 | 10/2008 | Esch |
| 7,453,646 | B2 | 11/2008 | Lo |
| 7,485,144 | B2 | 2/2009 | Esch |
| 7,494,505 | B2 | 2/2009 | Kappelhof et al. |
| 7,675,686 | B2 | 3/2010 | Lo et al. |
| 7,753,953 | B1 | 7/2010 | Yee |
| 7,759,408 | B2 | 7/2010 | Schorzman et al. |
| 7,763,069 | B2 | 7/2010 | Brady et al. |
| 7,776,088 | B2 | 8/2010 | Shadduck |
| 7,878,655 | B2 | 2/2011 | Salvati et al. |
| 7,971,997 | B2 | 7/2011 | Hiramatsu et al. |
| 7,988,290 | B2 | 8/2011 | Campbell et al. |
| 7,988,292 | B2 | 8/2011 | Neal et al. |
| 7,988,293 | B2 | 8/2011 | Raymond et al. |
| 8,162,927 | B2 | 4/2012 | Peyman |
| 8,246,631 | B2 | 8/2012 | Pynson |
| 2001/0001836 | A1 | 5/2001 | Cumming |
| 2001/0016771 | A1 | 8/2001 | Cumming |
| 2001/0039449 | A1 | 11/2001 | Johnson et al. |
| 2002/0046783 | A1 | 4/2002 | Johnson et al. |
| 2002/0055777 | A1 | 5/2002 | Cumming et al. |
| 2002/0072795 | A1 | 6/2002 | Green |
| 2002/0095212 | A1 | 7/2002 | Boehm |
| 2002/0107568 | A1 | 8/2002 | Zadno-Azizi et al. |
| 2002/0111678 | A1 | 8/2002 | Zadno-Azizi et al. |
| 2002/0116057 | A1 | 8/2002 | Ting et al. |
| 2002/0116058 | A1 | 8/2002 | Zadno-Azizi et al. |
| 2002/0116059 | A1 | 8/2002 | Zadno-Azizi et al. |
| 2002/0116060 | A1 | 8/2002 | Nguyen et al. |
| 2002/0116061 | A1 | 8/2002 | Zadno-Azizi et al. |
| 2002/0133167 | A1 | 9/2002 | Harish et al. |
| 2002/0133228 | A1 | 9/2002 | Sarver |
| 2002/0161434 | A1 | 10/2002 | Laguette et al. |
| 2002/0161435 | A1 | 10/2002 | Portney |
| 2002/0177896 | A1 | 11/2002 | Israel |
| 2002/0193876 | A1 | 12/2002 | Lang et al. |
| 2003/0003295 | A1 | 1/2003 | Dreher et al. |
| 2003/0004569 | A1 | 1/2003 | Haefliger |

(56) References Cited

U.S. PATENT DOCUMENTS

| | | |
|---|---|---|
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint, Jr. et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0186868 A1 | 9/2004 | Kim |
| 2004/0193263 A1 | 9/2004 | Bryan |
| 2004/0230203 A1 | 11/2004 | Yaguchi |
| 2004/0267359 A1 | 12/2004 | Makker et al. |
| 2005/0021139 A1 | 1/2005 | Shadduck |
| 2005/0033308 A1 | 2/2005 | Callahan et al. |
| 2005/0038446 A1 | 2/2005 | Vanderbilt et al. |
| 2005/0049606 A1 | 3/2005 | Vaquero et al. |
| 2005/0080484 A1 | 4/2005 | Marmo et al. |
| 2005/0113911 A1 | 5/2005 | Peyman |
| 2005/0125000 A1 * | 6/2005 | Tourrette et al. .............. 606/107 |
| 2005/0125055 A1 | 6/2005 | Deacon et al. |
| 2005/0125056 A1 | 6/2005 | Deacon et al. |
| 2005/0131535 A1 | 6/2005 | Woods |
| 2005/0143750 A1 | 6/2005 | Vaquero |
| 2005/0143751 A1 | 6/2005 | Makker et al. |
| 2005/0147735 A1 | 7/2005 | Lowery et al. |
| 2005/0149057 A1 | 7/2005 | Rathert |
| 2005/0165410 A1 | 7/2005 | Zadno-Azizi et al. |
| 2005/0222577 A1 | 10/2005 | Vaquero |
| 2005/0222578 A1 | 10/2005 | Vaquero |
| 2005/0222579 A1 | 10/2005 | Vaquero et al. |
| 2005/0251253 A1 | 11/2005 | Gross |
| 2005/0251254 A1 | 11/2005 | Brady et al. |
| 2005/0259221 A1 | 11/2005 | Marmo |
| 2005/0264756 A1 | 12/2005 | Esch |
| 2005/0283162 A1 | 12/2005 | Stratas |
| 2005/0283164 A1 | 12/2005 | Wu et al. |
| 2006/0020267 A1 | 1/2006 | Marmo |
| 2006/0020268 A1 | 1/2006 | Brady et al. |
| 2006/0069433 A1 | 3/2006 | Nun |
| 2006/0085013 A1 | 4/2006 | Dusek et al. |
| 2006/0097413 A1 | 5/2006 | Ghazizadeh et al. |
| 2006/0100703 A1 | 5/2006 | Evans et al. |
| 2006/0116763 A1 | 6/2006 | Simpson |
| 2006/0129129 A1 | 6/2006 | Smith |
| 2006/0134173 A1 | 6/2006 | Liu et al. |
| 2006/0135642 A1 | 6/2006 | Makker et al. |
| 2006/0142780 A1 | 6/2006 | Pynson et al. |
| 2006/0142781 A1 | 6/2006 | Pynson et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Ben Nun |
| 2007/0265636 A1 | 11/2007 | Huynh |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0058830 A1 | 3/2008 | Cole et al. |
| 2008/0065096 A1 | 3/2008 | Kappelhof et al. |
| 2008/0071286 A1 | 3/2008 | Kobayashi et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200921 A1 | 8/2008 | Downer |
| 2008/0200982 A1 | 8/2008 | Your |
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0018512 A1 | 1/2009 | Charles |
| 2009/0018548 A1 | 1/2009 | Charles |
| 2009/0024136 A1 | 1/2009 | Martin et al. |
| 2009/0027661 A1 | 1/2009 | Choi et al. |
| 2009/0030425 A1 | 1/2009 | Smiley et al. |
| 2009/0076602 A1 | 3/2009 | Ho et al. |
| 2009/0112313 A1 | 4/2009 | Mentak |
| 2009/0118739 A1 | 5/2009 | Kappelhof et al. |
| 2009/0124773 A1 | 5/2009 | Zhou et al. |
| 2009/0149952 A1 | 6/2009 | Shadduck |
| 2009/0171366 A1 | 7/2009 | Tanaka |
| 2009/0204123 A1 | 8/2009 | Downer |
| 2009/0228101 A1 | 9/2009 | Zadno-Azizi |
| 2009/0234366 A1 | 9/2009 | Tsai et al. |
| 2009/0234449 A1 | 9/2009 | De Juan, Jr. et al. |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0318933 A1 | 12/2009 | Anderson |
| 2010/0016963 A1 | 1/2010 | Park |
| 2010/0039709 A1 | 2/2010 | Lo |
| 2010/0063588 A1 | 3/2010 | Park |
| 2010/0094412 A1 | 4/2010 | Wensrich |
| 2010/0131058 A1 | 5/2010 | Shadduck |
| 2010/0161049 A1 | 6/2010 | Inoue |
| 2010/0179653 A1 | 7/2010 | Argento et al. |
| 2010/0228344 A1 | 9/2010 | Shadduck |
| 2010/0228346 A1 | 9/2010 | Esch |
| 2010/0324671 A1 | 12/2010 | Shadduck |

(56) References Cited

U.S. PATENT DOCUMENTS

| | | |
|---|---|---|
| 2010/0324672 A1 | 12/2010 | Esch et al. |
| 2011/0052020 A1 | 3/2011 | Hildebrand et al. |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0226351 A1 | 9/2012 | Peyman |
| 2012/0253458 A1 | 10/2012 | Geraghty et al. |
| 2012/0253459 A1 | 10/2012 | Reich et al. |
| 2013/0053954 A1 | 2/2013 | Rao et al. |
| 2013/0060331 A1 | 3/2013 | Shadduck |
| 2013/0103146 A1 | 4/2013 | Smiley et al. |
| 2013/0131794 A1 | 5/2013 | Smiley et al. |

FOREIGN PATENT DOCUMENTS

| | | |
|---|---|---|
| EP | 1332731 B1 | 8/2007 |
| EP | 1659991 B1 | 5/2009 |
| EP | 2060243 A1 | 5/2009 |
| EP | 2346441 B1 | 3/2013 |
| FR | 2784575 | 4/2000 |
| JP | 07-044938 | 5/1995 |
| JP | 8224295 w | 9/1996 |
| JP | 9294754 | 11/1997 |
| JP | 10-206609 | 8/1998 |
| JP | 11056998 w | 3/1999 |
| JP | 11276509 | 10/1999 |
| JP | 2003530978 w | 10/2003 |
| JP | 2008307394 A | 12/2008 |
| SU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/072689 A2 | 8/2004 |
| WO | WO 2005/018504 A1 | 3/2005 |
| WO | WO 2005/084588 A1 | 9/2005 |
| WO | WO 2006/004707 A2 | 1/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/005692 A1 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO2007/138564 A1 | 12/2007 |
| WO | WO 2009/100322 A2 | 8/2009 |
| WO | WO 2009/154455 A1 | 12/2009 |
| WO | WO 2011/119334 A1 | 9/2011 |
| WO | WO2012/006186 A2 | 1/2012 |

OTHER PUBLICATIONS

Baughman et al., "Negative poisson's ratios for extreme states fo matter," Science, vol. 288, pp. 2018-2022, Jun. 16, 2000.

Baughman, "Avoiding the shrink," Nature, vol. 425, pp. 667, Oct. 16, 2003.

Conlisk, A. T. et al; Mass Transfer and Flow in Electrically Charged Micro-and Nano-channels; Analytical Chemistry, vol. 74; iss. 9; pp. 2139-2150; 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," Proceedings of the First Intl Conf. on Shape Memory and Superelastic Tech., Asilomar Conference Center, Pacific Grove, CA, USA, pp. 115-120, 1994.

Gruber et al.; Exhaustive soxhlet extraction for the complete removal of residual compounds . . . ; Journal of Biomedical Materials Research; vol. 53; No. 5; pp. 445-448; Mar. 2000.

Jeon et al., "Shape memory and nanostructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes et al., "Microbuckling instability in elastomeric cellular sollids," J. Materials Science, vol. 28, pp. 4667-4672, 1993.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2900, Mar. 26, 2001.

Lakes, "Lateral deformations in extreme matter," Science, vol. 288, pp. 1976, Jun. 2000; 3 pgs.

Lakes, "Negative poisson's ratio materials," Science, vol. 238, pp. 551, Oct. 23, 1987.

Lakes, "No contractile obligations," Nature, vol. 358, pp. 713-714, 1992.

Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; 2002.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Metcalfe et al., "Cold hibernated elastic memory foams for endovascular interventions," Biomaterials, vol. 24, pp. 491-497, 2003.

Qiao et al.; Bio-inspired accommodating fluidic intraocular lens; Optics Letters; vol. 34; No. 20; pp. 3214-3216; Oct. 15, 2009.

Rosales et al.; Pentacam Scheimpflug QuantitativeImaging of the Crystalline Lens andIntraocular Lens; J. Refractive Surgery; vol. 25; pp. 421-428; May 2009.

Takahashi et al., "Structure and properties of shape-memory polyurethane block copolymers," Journal of Applied Polymer Science, vol. 60, pp. 1061-1069, 1996.

Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.

Tobushi et al., "Thermomechanical properties of shape memory polymers of polyurethane series and their applications," Journal de Physique IV, Colloque C1, vol. 6, pp. 377-384, 1996.

Vass et al.; Prediction of pseudophakic capsular bag diameter based on biometric variables; J Cataract Refract Surg.; vol. 25; pp. 1376-1381; 1999.

Wang et al., "Deformation of extreme viscoelastic metals and composites," Materials Science and Enginerring A, vol. 370, pp. 41-49, 2004.

Wang et al., "Extreme stiffness systems due to negative stiffness elements," American Journal of Physics, vol. 72, No. 1, pp. 40-50, Jan. 2004.

(56) References Cited

OTHER PUBLICATIONS

Wang et al., "Stable extremely-high-damping discrete viscoelastic systems due to native stiffness elements," Applied Physics Letters, vol. 84, No. 22, pp. 4451-4453, May 31, 2004.

Wyant et al; "Basic Wavefront Aberration Theory for Optical Metrology," Applied Optics and Optical Engineering, vol. XI, 1992: pp. 1, 28-39.

Xu et al., "Basic negative poisson's ratio microstructures by soft lithography," Advanced Materials, vol. 11, No. 14, 1999, pp. 1186-1189, 1999.

Scholl et al.; U.S. Appl. No. 13/193,487 entitled "Accommodating Intraocular Lenses," filed Jul. 28, 2011.

Smiley et al.; U.S. Appl. No. 13/193,983 entitled "Accommodating Intraocular Lenses," filed Jul. 29, 2011.

Smiley et al.; U.S. Appl. No. 13/194,004 entitled "Accommodating Intraocular Lenses," filed Jul. 29, 2011.

Shadduck, John H.; U.S. Appl. No. 13/300,245 entitled "Accommodating Intraocular Lenses and Methods of Use," filed Nov. 18, 2011.

Lakes; Deformations in extreme matter; Science; perspectives; vol. 288; No. 5473; pp. 1976-1977; Jun. 16, 2000.

Langenbucher et al., "Computerized calculation scheme for toric intraocular lenses," Acta Ophthalmologica Scandinavica, vol. 82, No. 3, pp. 270-276, Jun. 2004.

Matthews et al.; U.S. Appl. No. 13/835,876 entitled "Intraocular Lens Delivery Systems and Methods of Use," filed Mar. 15, 2013.

* cited by examiner

INTRAOCULAR LENS DELIVERY DEVICES AND METHODS OF USE

CROSS-REFERENCE

This application claims the benefit of U.S. Provisional Application No. 61/363,155, filed Jul. 9, 2010, which is incorporated herein by reference in its entirety.

BACKGROUND OF THE INVENTION

Intraocular lens delivery systems have been developed but have several shortcomings. To implant an intraocular lens into an eye, an incision needs to be made in the eye to allow for passage of a delivery device and/or the intraocular lens. In general, it is desirable to make the incision is small as possible to cause the least amount of damage to the eye and shorten the healing process. Depending on the configuration and/or size of the intraocular lens, some intraocular lenses need to be deformed, sometimes controllably, into a smaller delivery profile so they will fit through the incision and into the eye. Delivery devices and/or systems are needed that can controllably deform or alter the configuration or orientation of the intraocular lens for delivery through an incision in an eye.

SUMMARY OF THE INVENTION

One aspect of the disclosure is an intraocular lens delivery system, comprising a delivery device with a port therein adapted to receive a cartridge; and a cartridge adapted to receive an intraocular lens therein, the cartridge having a leading haptic receiving area and a trailing haptic receiving area. The port can be a side port, and the delivery device can further comprise a positioning element to align the cartridge and delivery device at a predetermined position.

In some embodiments the cartridge comprises a channel adapted to be in communication with a channel within the delivery device. The cartridge can include an optic receiving area, and wherein the delivery device channel, the cartridge channel, and the optic receiving area are all in fluid communication.

In some embodiments the delivery device includes a first actuator adapted to load an intraocular lens into a distal loading portion of the delivery device, and a second actuator adapted to control a second delivery element to deploy the intraocular lens from the distal loading portion.

One aspect of the disclosure is a cartridge adapted to receive an intraocular lens therein, comprising a first portion with an optic receiving area, a leading haptic receiving area, and a trailing haptic receiving area; and a second portion coupled to the first portion and adapted to be in open and closed positions relative to the first portion.

In some embodiments the second portion has a complimentary optic portion receiving area, a leading haptic receiving area, and a trailing haptic receiving area. The first portion and second portion can be coupled at a hinge. In some embodiments the leading haptic receiving area is distal to the optic receiving area. In some embodiments the trailing haptic receiving area is disposed to the side of the optic receiving area. In some embodiments the cartridge further comprises a channel in communication with the optic receiving area. The channel can be disposed proximal to the optic receiving area.

One aspect of the disclosure is a delivery device adapted to deliver an intraocular lens, comprising an elongate body with a lumen therein; a plunger disposed within the elongate body and adapted to move axially with respect to the elongate body; and an actuator adapted to prime a fluid delivery assembly and dispense a fluid through a fluid channel within the elongate body.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION OF THE INVENTION

One aspect of the disclosure is a delivery system including a delivery device adapted to receive a cartridge therein. The cartridge is adapted to receive an intraocular lens. In use, the delivery system delivers the intraocular lens from the cartridge and the delivery device and into an eye.

Figure 1A:
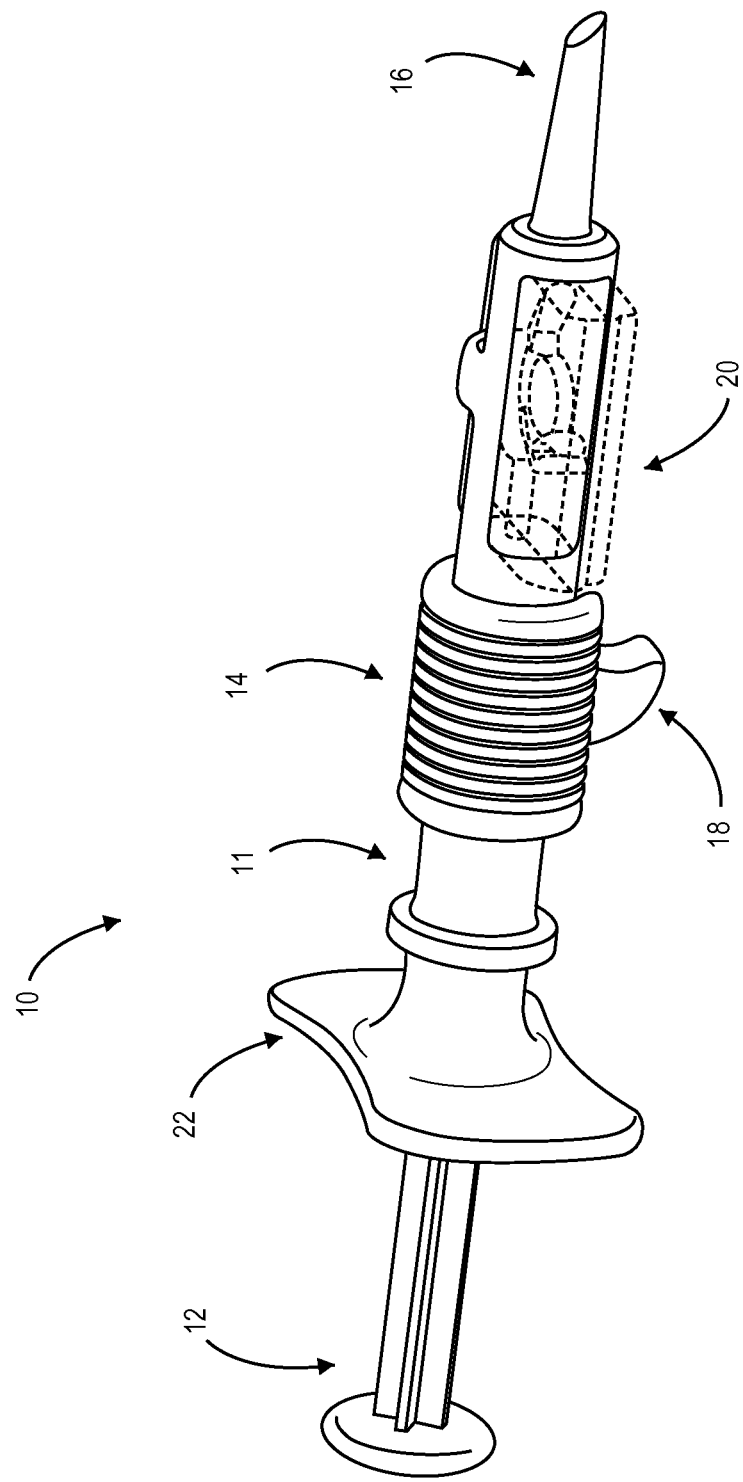
FIGS. 1A-1C illustrate an exemplary delivery system including a delivery device and cartridge.
Figure 1B:
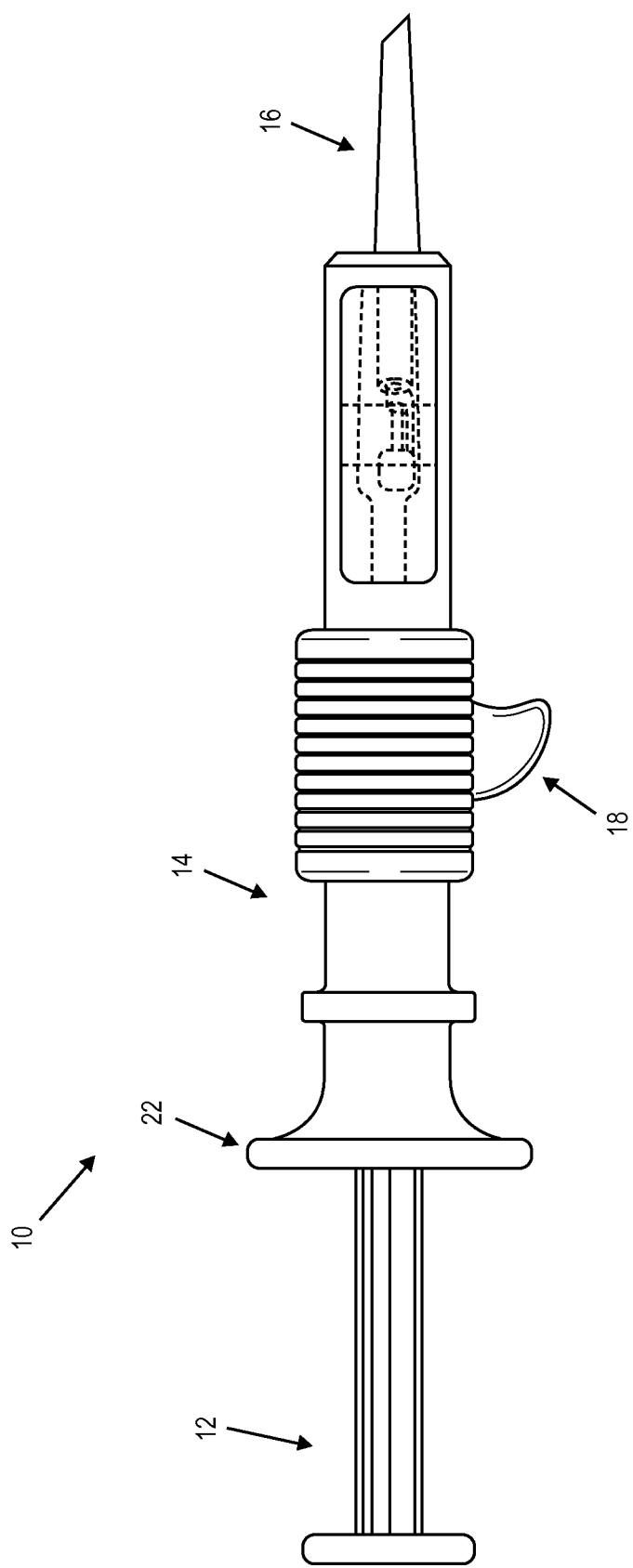
Figure 1C:
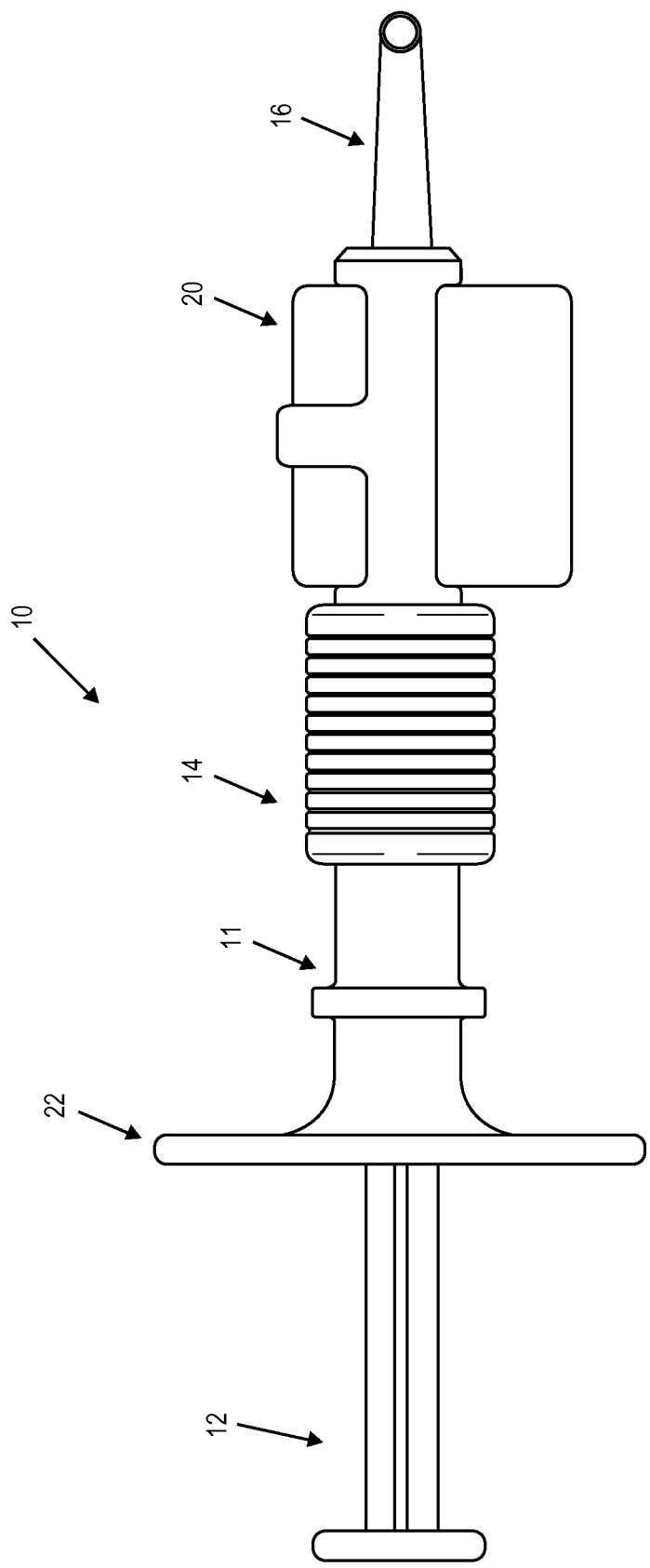

FIGS. 1A-1C show an exemplary system including delivery device 10 and cartridge 20 disposed therein. An intraocular lens is not show in the cartridge for clarity, and a variety of intraocular lenses could be used with the systems herein. Delivery device 10 includes elongate body 11 extending between proximal portion 22 and distal portion 16. Elongate body 11 is adapted to receive plunger 12 therein, such that device functions similarly to a syringe. Elongate body 11 includes a port extending therethrough, adapted to receive cartridge 20. Device 10 also includes first actuator 14 and second actuator 18, the latter in the form of a trigger. Distal portion 16 is in the form of a nozzle with a distal port from which the intraocular lens is deployed. In this embodiment the distal port has a beveled end. Distal portion 16 is also tapered towards the distal end. The cross section at the distal end is generally elliptical. FIGS. 1B and 1C show side view and bottom views, respectively, of cartridge 20 disposed within device 10.

Figure 2A:
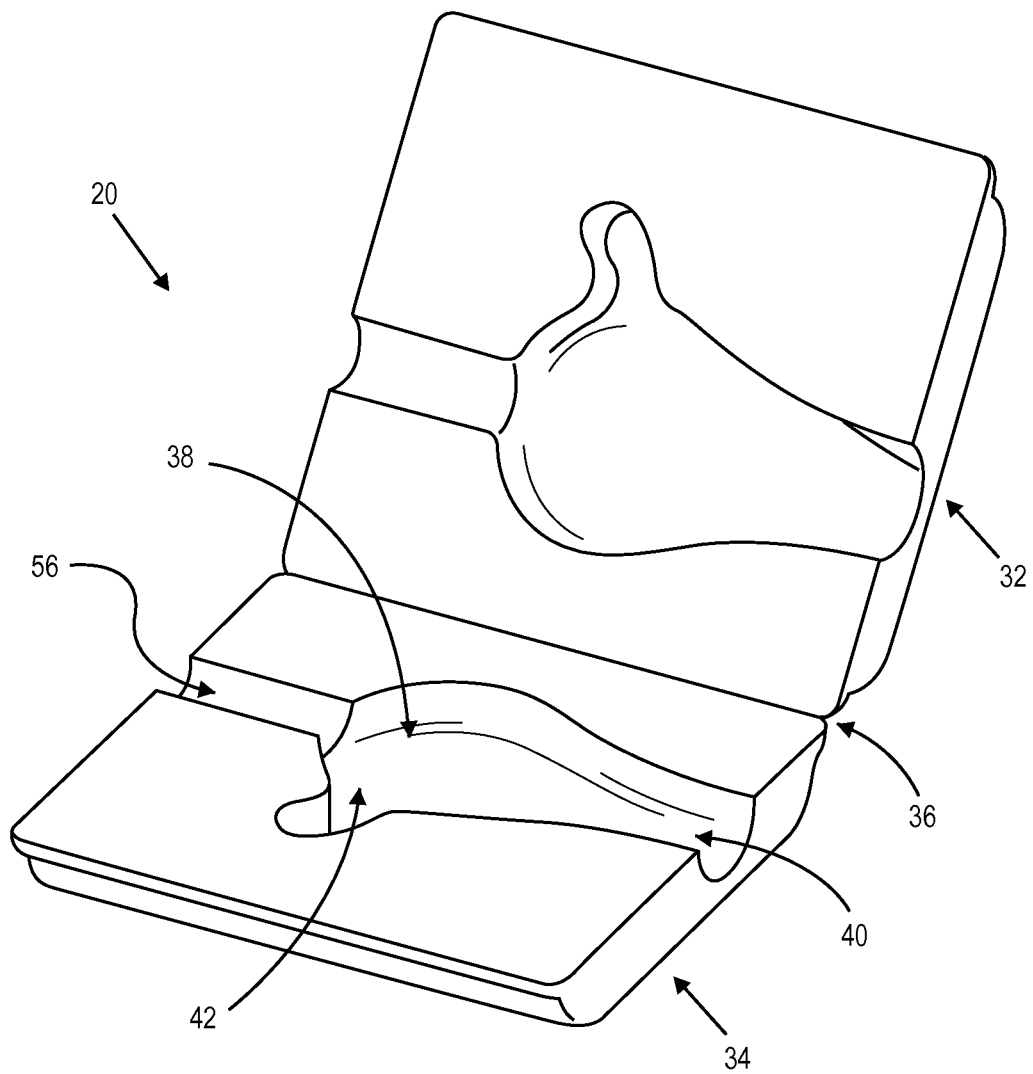
FIGS. 2A-2C illustrate an exemplary cartridge and intraocular lens.

FIG. 2A illustrates cartridge 20 in an open configuration and adapted to receive an intraocular lens therein. Cartridge 20 is hinged with a first portion 32 and a second portion 34 coupled by any type of hinge 36 (e.g., a living hinge). Cartridge 20 has been formed with an intraocular lens receiving area, which includes an optic portion receiving area 38, leading haptic receiving area 40, and trailing haptic receiving area 42. In some embodiments the cartridge is molded with these areas formed therein. Cartridge also includes channel 56 disposed proximal to the lens receiving area, adapted to receive a portion of delivery system, a fluid, etc., therethrough.

Figure 2B:
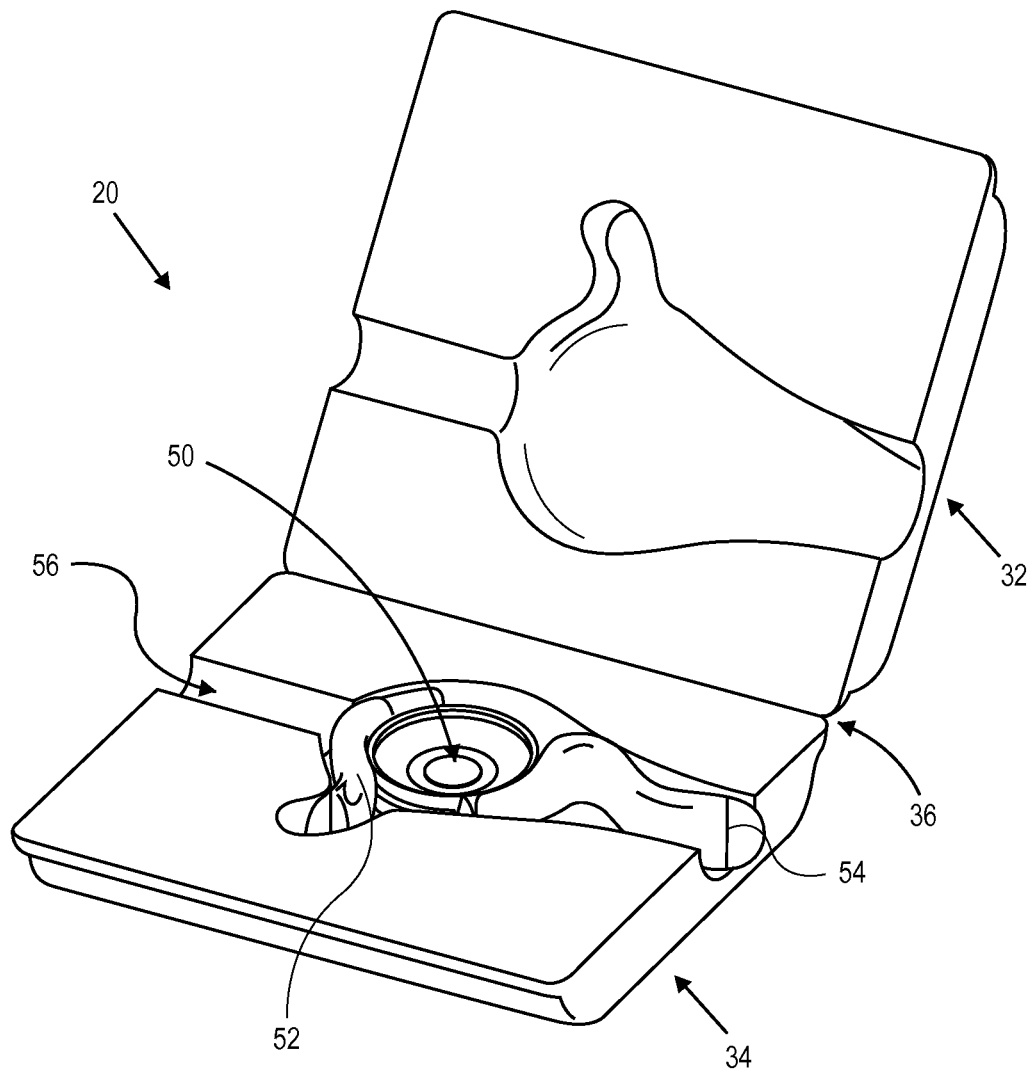

FIG. 2B shows an exemplary intraocular lens disposed within cartridge 20. In this embodiment, intraocular lens includes an optic portion 50 and haptics 52 and 54. Optic 50 has been positioned within optic receiving area 38, haptic 54 has been positioned within leading haptic receiving area 40, and haptic 52 has been positioned within trailing haptic receiving area 42. Haptic 54 is disposed distal to the optic 50, while haptic 52 is positioned generally to the side of optic 50, but could be disposed in any position relative to the optic. For example, haptic 52 could be positioned in a more trailing position if haptic receiving area 42 were formed in such a position.

In this exemplary embodiment, the intraocular lens is a fluid-driven intraocular lens, such as is described in US 2008/0306588, filed Jul. 22, 2008, the disclosure of which is incorporated by reference herein. Optic portion 50 is in fluid communication with haptics 52 and 54. Fluid distribution during delivery and other methods of use that can be incorporated into the systems herein can be found in US 2009/0030425, filed Jul. 23, 2008, the disclosure of which is incorporated by reference herein.

Figure 2C:
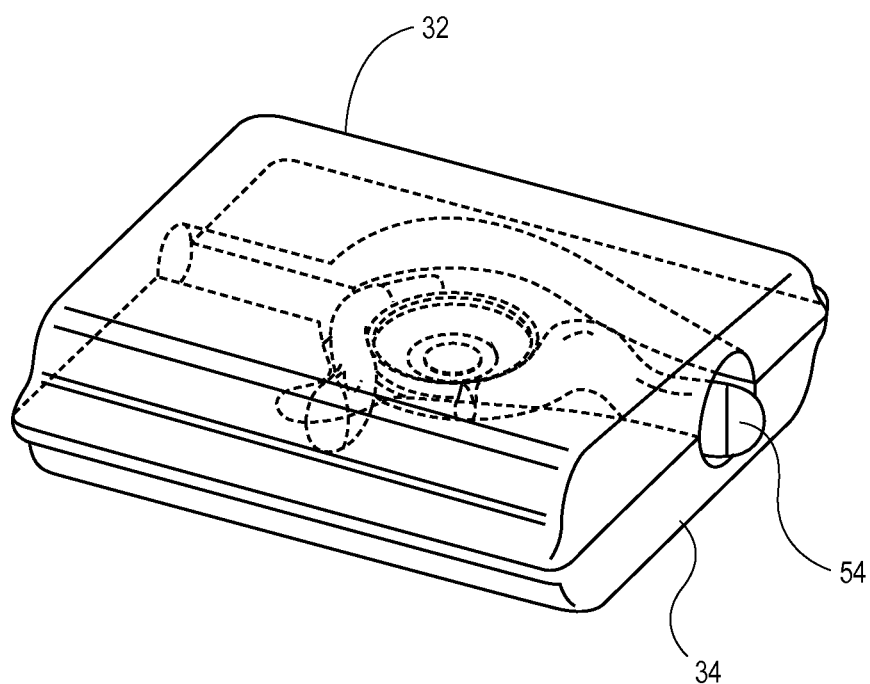

In FIG. 2C, first portion 32 has been closed relative to second portion 34 such that the cartridge is in a closed position, ready to be positioned within delivery device 10. When portion 32 is closed, some of the fluid within the lens may be slightly redistributed within the lens, or it may not be.

Figure 3A:
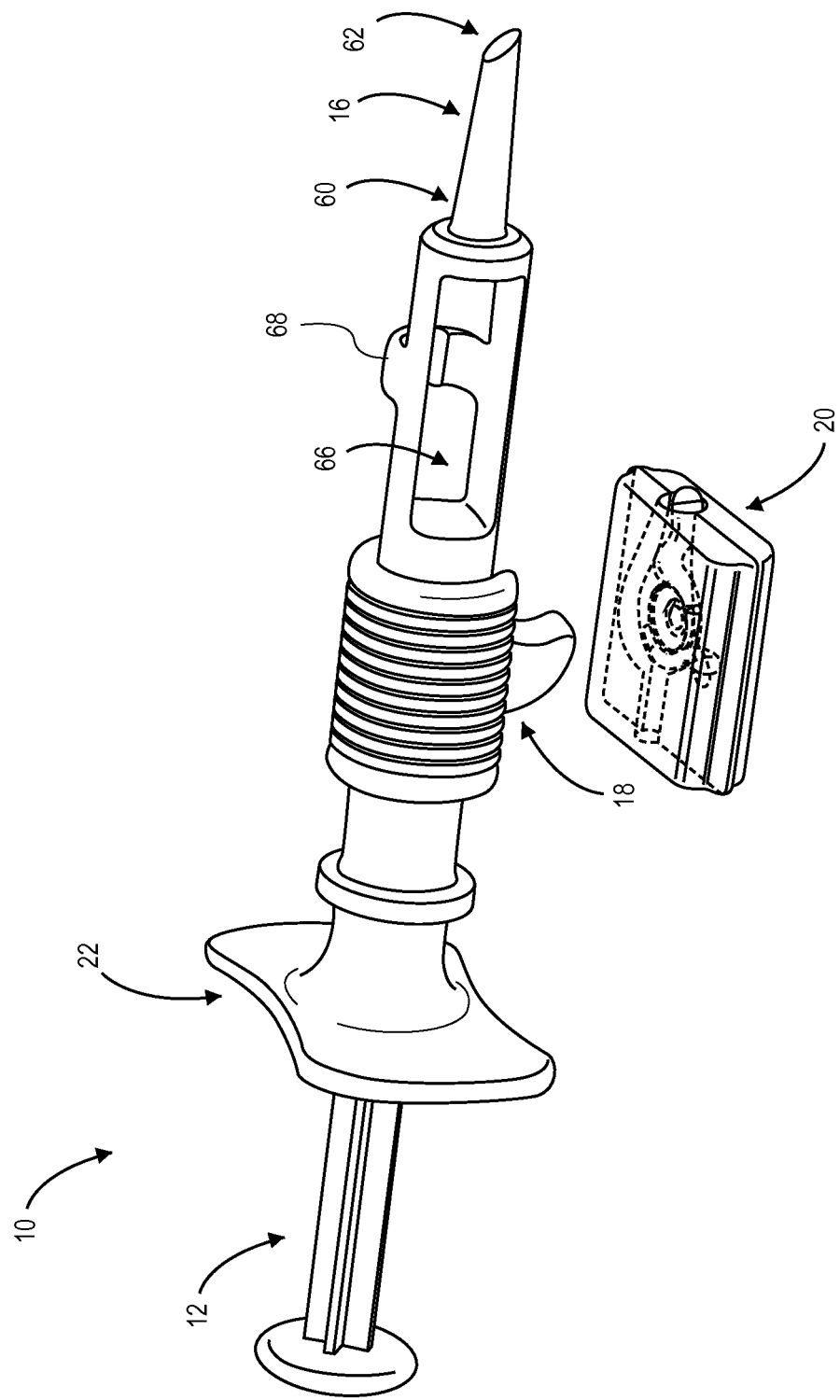
FIGS. 3A-3E illustrate an exemplary method of delivering an intraocular lens using the delivery device and cartridge.

FIG. 3A illustrates cartridge 20 with an intraocular lens disposed therein, and delivery device 10, including port 66 adapted to receive cartridge 20 therethrough. Device 10 also includes positioning element 68 adapted to maintain cartridge 20 at a predetermined position with respect to port 66. The positioning element 68 is positioned to align a channel within device 10 with channel 56 in cartridge 20. This allows a fluid, a portion of delivery device, etc., to be advanced through the delivery device and the cartridge to deploy the intraocular lens, as described below.

Figure 3B:
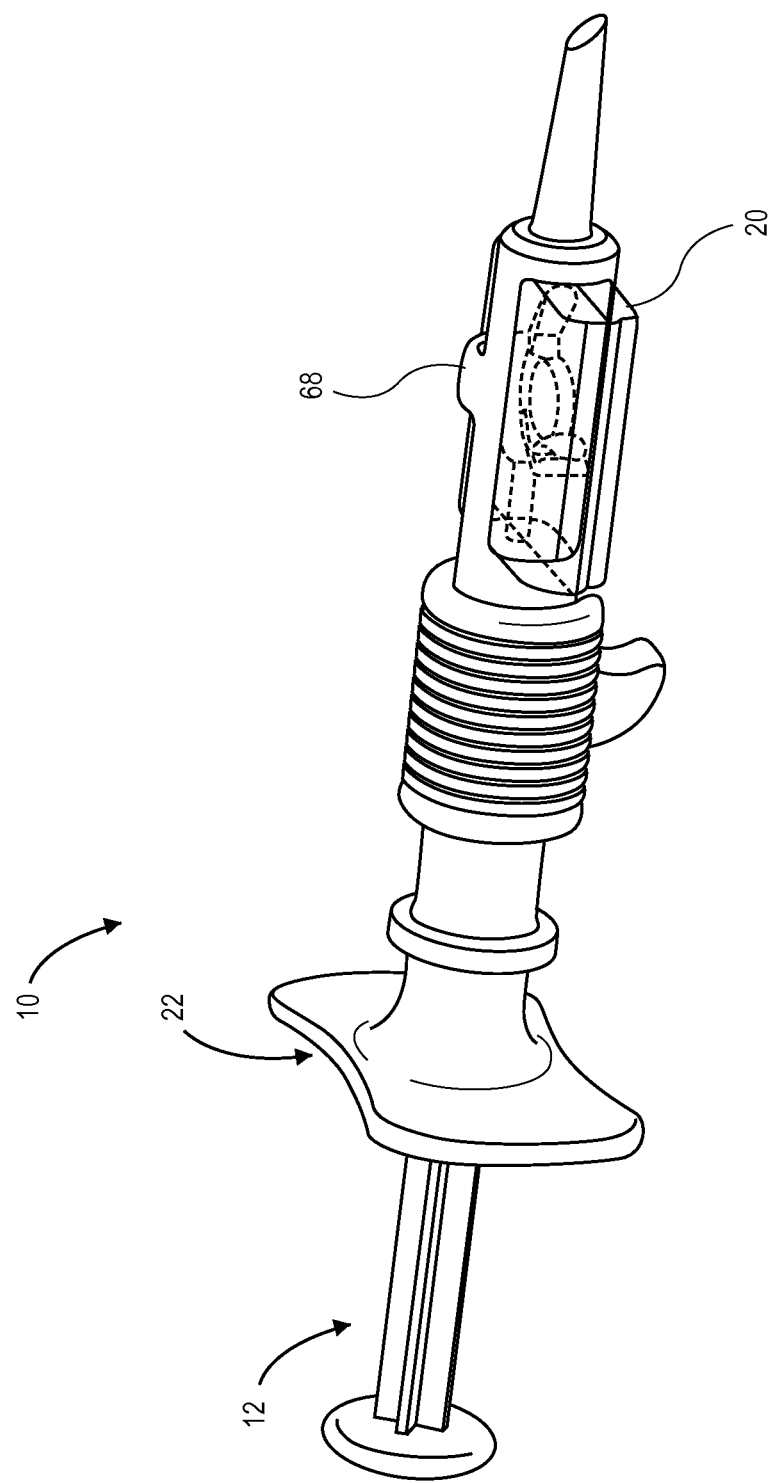
Figure 3C:
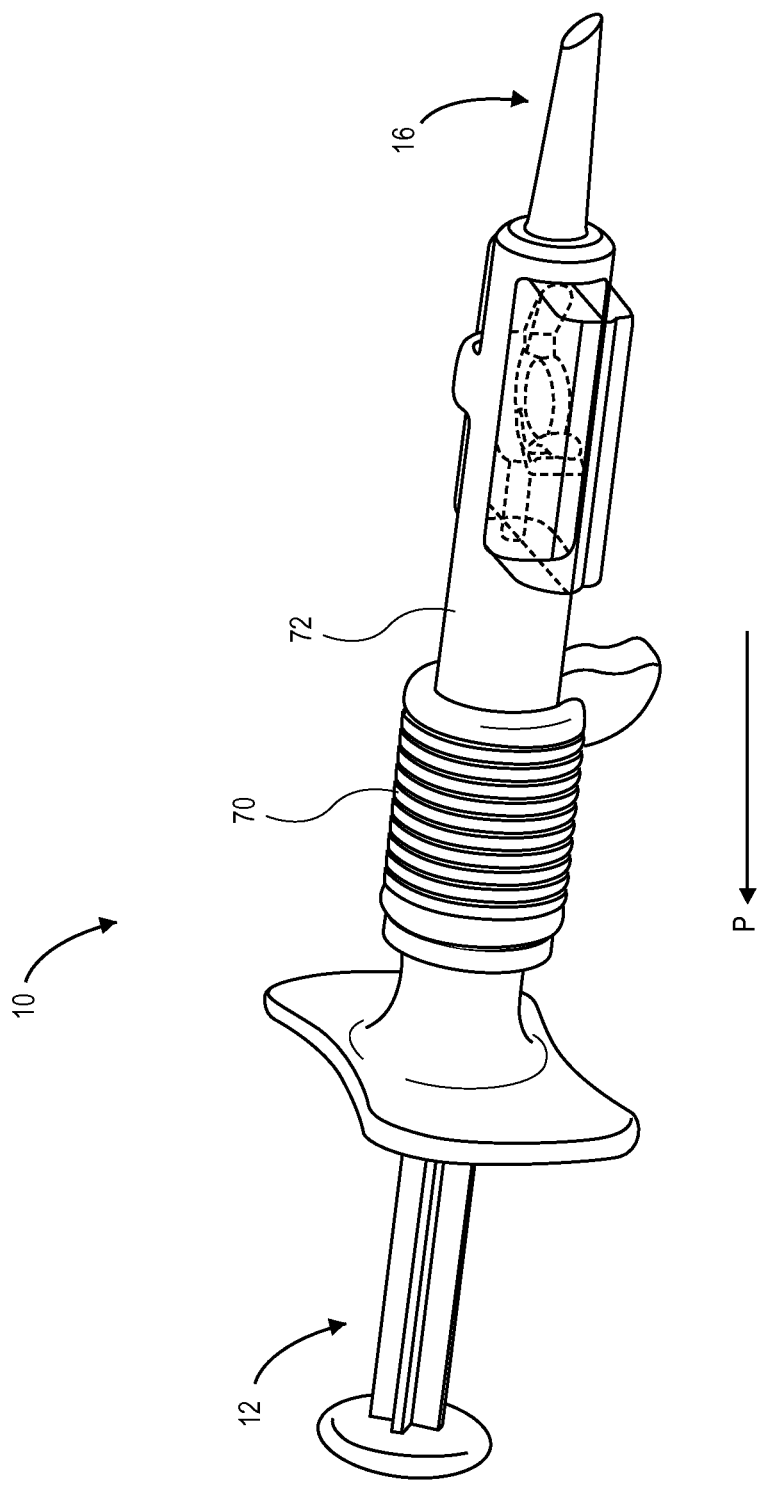

FIG. 3B shows cartridge 20 advanced through port 66 (which could also be a top port or bottom port) and engaging positioning element 68.

Figure 3D:
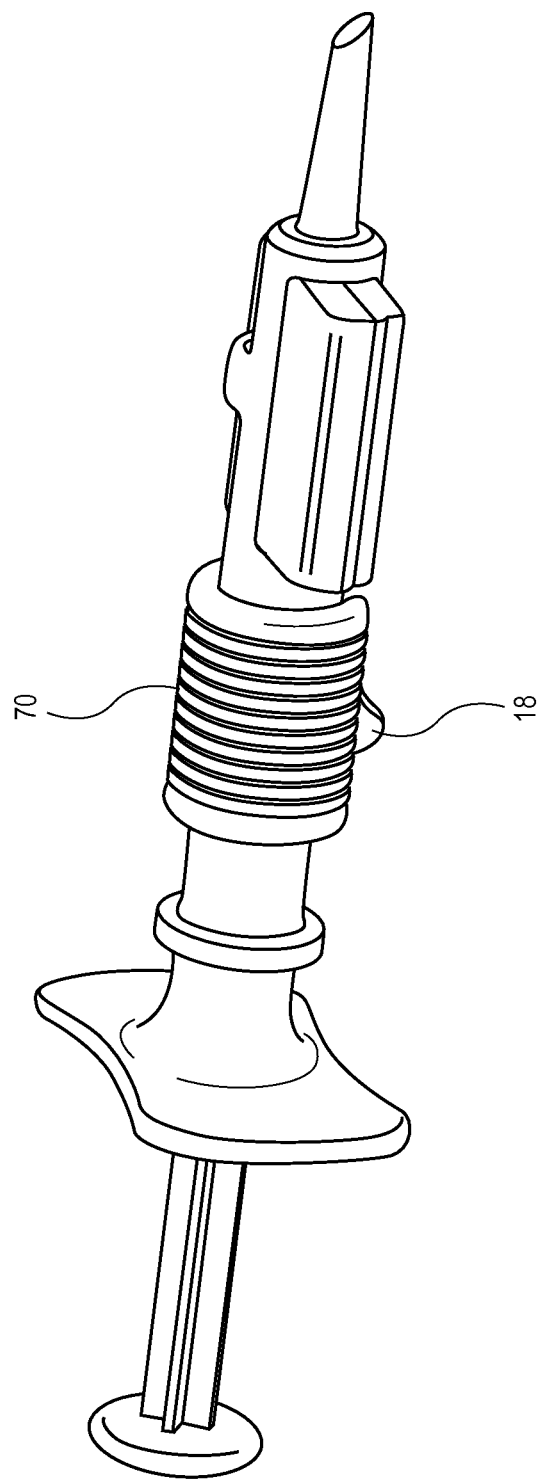

Actuator 70 is then retracted in the proximal direction ("P"), which activates, or primes, fluid delivery. In FIG. 3D, actuator 18 in the form of a trigger is actuated, causing actuator 70 to be advanced forward, moving a fluid (or mechanical component) through channel 56 in cartridge 20. This causes the intraocular lens to be advanced through cartridge and loaded into the nozzle of device 10. As is it being loaded, the haptics and/or optic are deformed into a delivery configuration. Positioning the haptics as described with respect to FIGS. 2A-2C, the leading haptic is first loaded, followed by the optic, and then by the trailing haptic. This configuration eases the loading on the lens. While actuation of actuator 18 can move a fluid through the system to load the lens, actuating actuator 18 can alternatively or in addition to move a piston or plunger component that engages and pushes the lens into the nozzle. The plunger can be adapted to engage the optic, bypassing the trailing haptic.

Figure 3E:
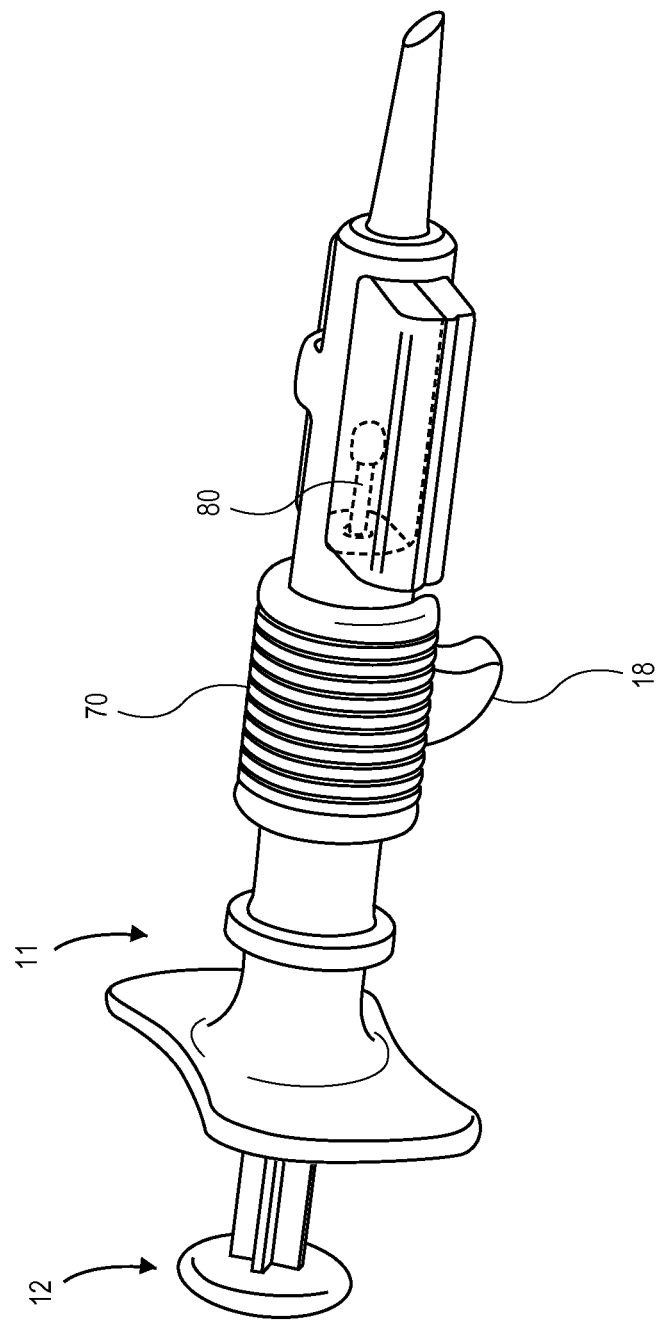

In FIG. 3E, plunger 12 is advanced with respect to body 11 and within body 11, causing plunger 80 to be advanced relative to body 11 and to the intraocular lens. This plunger is advanced until it engages with the lens and drives it out of the nozzle and into an eye.

Intraocular lenses with different configurations can be delivered with the cartridges and delivery devices herein, as long as the cartridge is adapted to receive them. For example, the cartridge may need to be molded in a different way to receive a different intraocular lens.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. An intraocular lens delivery system, comprising:
   an intraocular lens comprising a leading haptic and a trailing haptic;
   a delivery device with a port therein adapted to receive a cartridge; and
   a cartridge adapted to receive the intraocular lens therein, the cartridge having a leading haptic receiving area and a trailing haptic receiving area, and a distal port through which the intraocular lens passes,
   wherein the intraocular lens and the cartridge are configured so that the leading haptic and the trailing haptic can be simultaneously maintained in deformed configurations, the leading haptic receiving area disposed distal to the trailing haptic receiving area such that the leading haptic is delivered out of distal port before the trailing haptic, wherein the distal port has a smaller width than a diameter of an optic portion of the intraocular lens.

2. The system of claim 1 wherein the port is a side port, the delivery device further comprising a positioning element to align the cartridge and delivery device at a predetermined position.

3. The system of claim 1 wherein the cartridge comprises a channel adapted to be in communication with a channel within the delivery device.

4. The system of claim 3 wherein the cartridge includes an optic receiving area, and wherein the delivery device channel, the cartridge channel, and the optic receiving area are all in fluid communication.

5. The system of claim 1 wherein the delivery device includes a first actuator adapted to load an intraocular lens into a distal loading portion of the delivery device, and a second actuator adapted to control a second delivery element to deploy the intraocular lens from the distal loading portion.

6. The system of claim 1 wherein the leading haptic receiving area comprises a tapered portion.

* * * * *